US006714622B2

(12) United States Patent
Horbaschek

(10) Patent No.: US 6,714,622 B2
(45) Date of Patent: Mar. 30, 2004

(54) METHOD AND APPARATUS FOR PRODUCING AN OVERALL IMAGE FROM A NUMBER OF PARTIAL IMAGES

(75) Inventor: Heinz Horbaschek, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/199,249

(22) Filed: Jul. 19, 2002

(65) Prior Publication Data
US 2003/0016787 A1 Jan. 23, 2003

(30) Foreign Application Priority Data

Jul. 20, 2001 (DE) .......................... 101 34 651

(51) Int. Cl.[7] .................................. H05G 1/64
(52) U.S. Cl. ..................... 378/98.12; 378/98; 378/62; 348/218.1; 348/77
(58) Field of Search ................. 378/98, 98.12, 378/62; 600/410, 425, 407; 348/218.1, 77, 584; 382/284, 291, 294

(56) References Cited

U.S. PATENT DOCUMENTS

| | | | |
|---|---|---|---|
| 5,617,461 A | | 4/1997 | Schreiner ............... 378/98.5 |
| 5,631,942 A | * | 5/1997 | Shinoda ............... 378/98.12 |
| 5,974,113 A | * | 10/1999 | Bruijns et al. ............. 378/98.7 |
| 5,986,279 A | * | 11/1999 | Dewaele ............... 250/582 |
| 6,215,848 B1 | * | 4/2001 | Linders et al. ............ 378/98.12 |
| 6,437,306 B1 | * | 8/2002 | Melen ............... 250/208.1 |
| 6,459,094 B1 | * | 10/2002 | Wang et al. ............ 250/584 |
| 6,549,681 B1 | * | 4/2003 | Takiguchi et al. .......... 382/294 |
| 6,571,022 B2 | * | 5/2003 | Okisu et al. ............ 382/294 |
| 6,594,403 B1 | * | 7/2003 | Bozdagi et al. ............ 382/284 |
| 6,628,751 B2 | * | 9/2003 | Eikenberg ............ 378/98.12 |

FOREIGN PATENT DOCUMENTS

| | | |
|---|---|---|
| DE | 43 10 993 A1 | 10/1994 |
| DE | 195 27 148 C1 | 1/1997 |
| DE | 197 35 112 A1 | 2/1999 |
| WO | WO 01/52190 A1 | 7/2001 |

* cited by examiner

Primary Examiner—Craig E Church
Assistant Examiner—Jurie Yun
(74) Attorney, Agent, or Firm—Schiff Hardin LLP

(57) ABSTRACT

In a method and apparatus for producing an overall image from a number of partial images which are produced successively for common playback, a first partial image is produced and stored, and at least a portion of the first partial image, that adjoins a second partial image to be produced, is played back. A survey image is produced for the second partial image and this survey image is simultaneously played back with the first partial image, with overlapping regions adjoining each other. From this simultaneous playback, the correct orientation of the exposure region for the second partial image is selected, and the image acquisition device is correspondingly positioned and the second partial image is produced, The first and second partial images are then joined to form the overall image.

8 Claims, 4 Drawing Sheets

METHOD AND APPARATUS FOR PRODUCING AN OVERALL IMAGE FROM A NUMBER OF PARTIAL IMAGES

BACKGROUND OF THE INVENTION

1. Field of the Invention

The present invention is directed to a method for producing an overall image from a number of partial images to be produced successively for common playback, and also is directed to an apparatus for implementation of the method. Such a method serves the purpose of matching images for the acquisition.

2. Description of the Prior Art

The format of X-ray film or of an image converter, such as a solid-state image converter or X-ray image intensifier, is not adequate for various radiological investigations.

In these instances, for example given a "spine presentation", a number of exposures are made successively, the respective, resulting images then being electronically joined by means of a software program. The aiming device of the X-ray apparatus travels the length of the body region to be presented—the spinal column—for the exposures in this example, with an entire series of narrow images being made during this motion, and which are then combined with a specific software program at, for example, a workstation.

The spinal column thus can be presented as a whole and certain geometrical measurements can be implemented using specific measurement programs.

The apparatus motion in the exposure is synchronized with the image acquisition frequency, so that the registered partial images can be joined to one another without significant X-Y shifting.

A smaller X-ray detector, that may be too small for standard exposures, is usually employed in a lightweight and mobile apparatus.

A targeted control of the device for the registration of the partial images that is required for the composing, however, is not possible in the case of mobile apparatus.

When formats that are larger than the format of the X-ray detector are required, the manual registration of defined partial images is nearly impossible because overlaps, gaps or rotation or even variations in size that are too significant can arise between the partial images in the exposure.

SUMMARY OF THE INVENTION

An object of the present invention is to provide a method and an apparatus of the type initially described with which an easy setting of the exposure field is enabled in the successive exposures.

This object is inventively achieved by a method having the following steps:

a) producing a first partial image;
b) storing the first partial image;
c) playing back at least a part of the first partial image that adjoins a second partial image to be produced;
d) producing a survey image for the second partial image;
e) simultaneously playing back the survey image and the first partial image, whereby overlapping regions adjoin one another;
f) selecting the correct attitude of the exposure region for the second partial image;
g) placing the image acquisition device;
h) producing a second partial image;
i) joining the partial images to form the overall image.

The steps c) through h) can be repeated as warranted for further images with the second partial image used as the first partial image and a further image used as the second image.

As a result, partial images that have already been shot can be consulted in order to be able to select the correct image excerpt for the following exposure currently being obtained. For example, the edge zone of the partial image already registered is mixed in and the current transillumination image then shows the image excerpt selected as the second partial image.

It has proven advantageous to divide the overall image into a number of windows and to insert the exposures that have already been shot in respectively attitudinally correct positions in a window.

Inventively, the survey image can be produced as a single shot in transillumination mode or in an acquisition mode.

Alternatively, a real image, for example a photograph of the patient, can be produced in addition to the partial image, as a survey image in exactly the same projection corresponding to that of the first partial image.

The inventive diagnostic apparatus has an image acquisition device, an image system and a playback device and the image system includes:

a) a first partial image store connected to the image acquisition device;
b) a shift device connected to the first partial image store for playing back at least a part of the first partial image that adjoins a second partial image to be produced;
c) a mixing device connected to the image acquisition device for survey images of further partial images in addition to the reproduced part of the partial images already produced;
d) further partial image stores that are connected to the mixing device; and
e) an arrangement for joining the partial images to form the overall image.

A control device for the alignment of the image acquisition device can be allocated to the image system.

DESCRIPTION OF THE PREFERRED EMBODIMENTS

Figure 1:
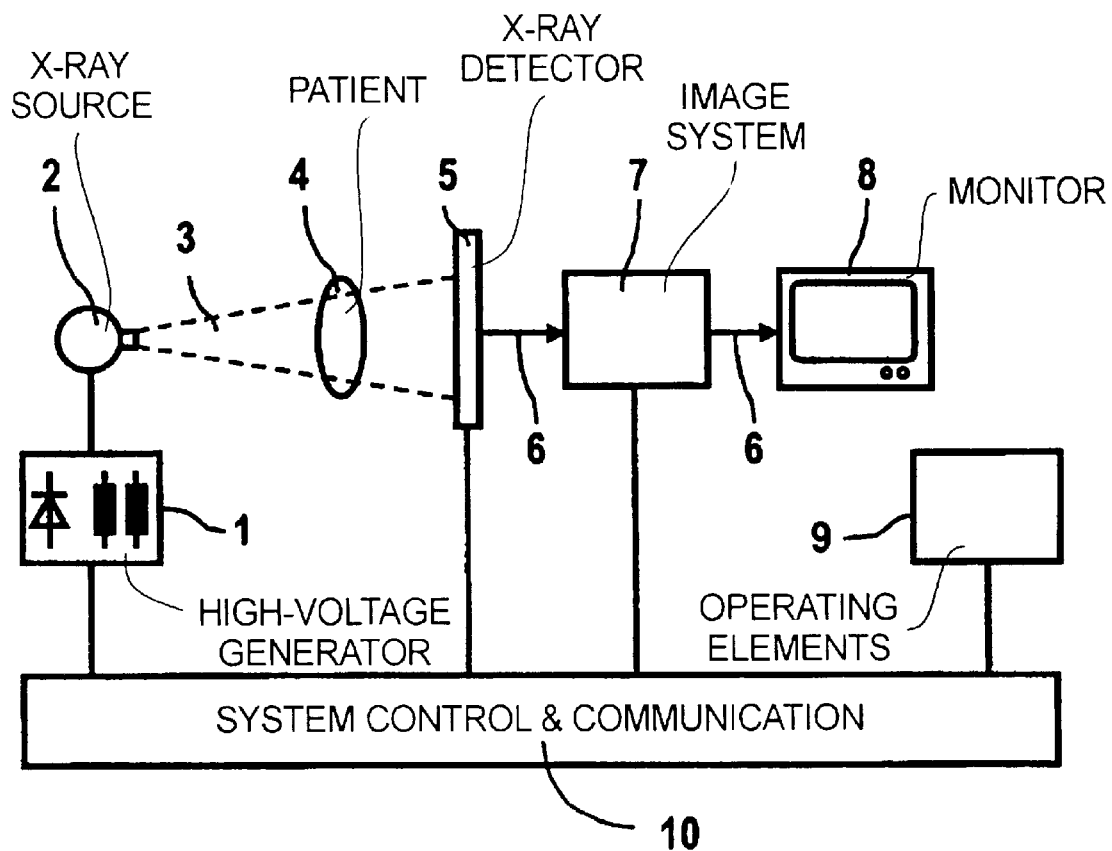
FIG. 1 is a block diagram of a known X-ray diagnostics installation.

FIG. 1 shows an X-ray diagnostics installation known from German PS 195 27 148 that has an X-ray tube 2 supplied with high-voltage and filament voltage by a high-voltage generator 1 that generates a conical X-ray beam 3 that penetrates a patient 4, so as to generate radiation images on an X-ray detector 5. The output signal of the X-ray detector 5, the image data 6, is supplied to an image system 7. The image system 7 can include converters, image memories and processing circuits. It is connected to a monitor 8 for the playback of the acquired X-ray images. Operating elements 9 are connected to the other components of the X-ray diagnostics installation via a system control and communication 10.

Figure 2:
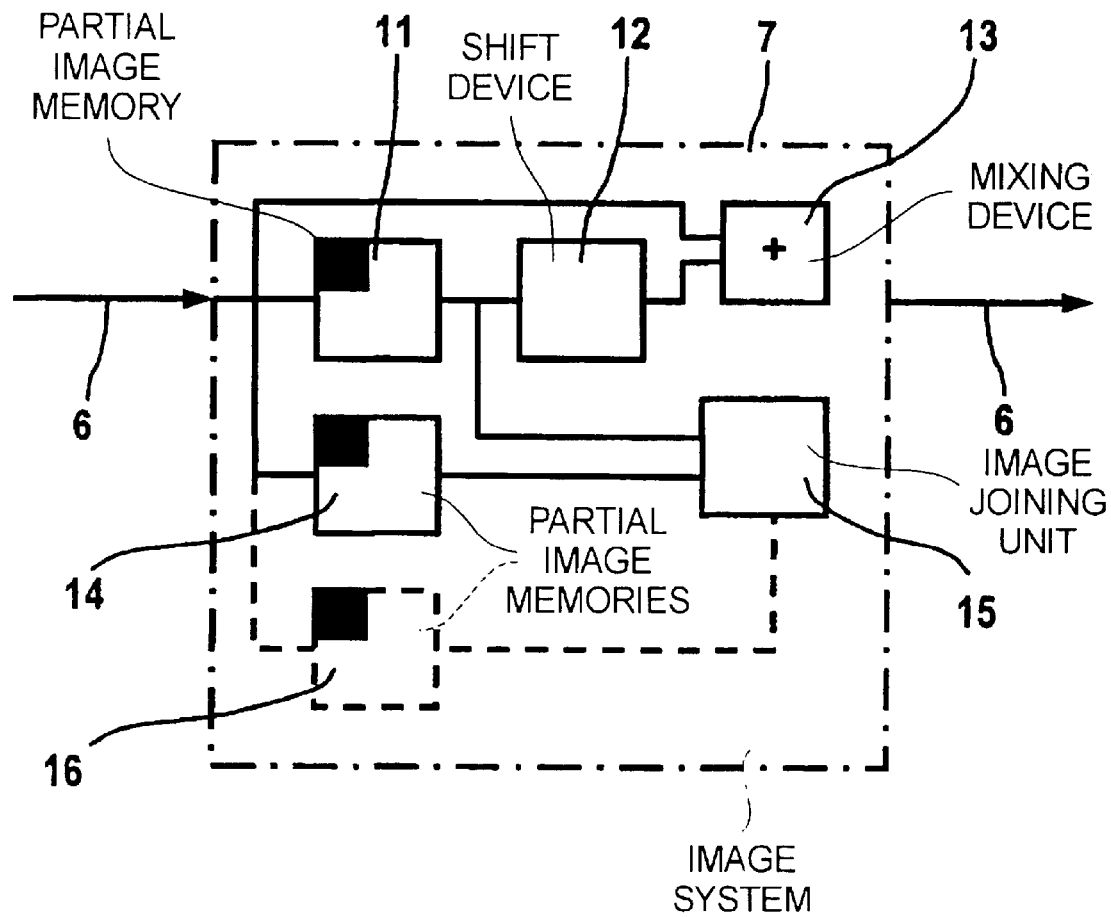
FIG. 2 is a block diagram of the inventive image system, which is used in the installation of FIG. 1.
Figure 3:
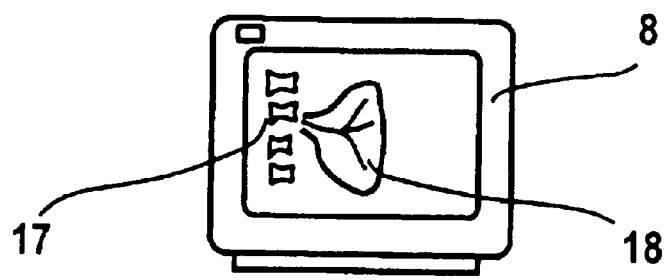
FIG. 3 shows a monitor image with a first partial image in accordance with the invention.

FIG. 2 shows a part of the image system 7 for the implementation of the inventive method. The image data 6 supplied by the X-ray detector 5 are supplied to a first partial image memory 11 that stores a first partial image that, for example, is shown in FIG. 3. The output signal of the first partial image memory 11 is supplied to a shift device 12 that—under operator control or automatically according to a pre-selection —shifts the first partial image such that only the edge region of the first partial image that adjoins a partial image to be subsequently registered is reproduced on the monitor 8, as can be seen from FIG. 4. The output of the shift device 12 is connected to a mixing device 13 to which the current image data 6 that arise from the current transillumination are supplied, so that the X-ray image shown in FIG. 5 is visible on the monitor 8. Alternatively, a single exposure can be employed instead of the transillumination images when a further image memory is arranged in this branch. Using the operating elements 9, or automatically by means of pre-selection of a region on the monitor 8, the X-ray apparatus can now be adjusted such that the second partial image exhibits only a slight overlap with the first partial image and both images exhibit the same alignment. When this adjustment event has been ended, a second partial image can be produced and stored in the second partial image memory 14. If the overall image is to be composed of only two partial images, then the procedure is complete, and the output signals of the two partial image memories 11 and 14 are supplied to a unit 15 for joining the partial images that produces a pixel-exact joining and superimposition of the two partial images, so that the overall image can be seen on the monitor 8 (FIG. 6).

If instead, the overall image is to be composed of a more than two partial images, then further partial image memory 16 can be provided that are consecutively filled, but care must be exercised to be sure that the preceding image that the current image adjoins is always stored in the first partial image memory 11, the data thereof being supplied to the mixing device 12.

Figure 4:
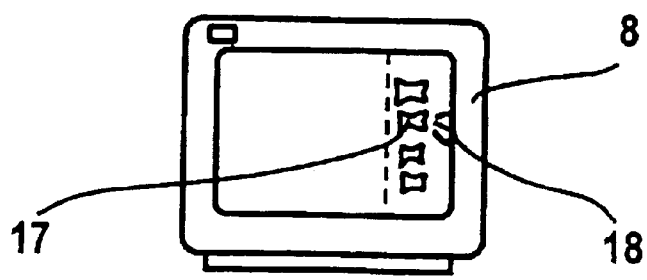
FIG. 4 shows monitor image after the exposure with a part of the shifted, first partial image in accordance with the invention.
Figure 5:
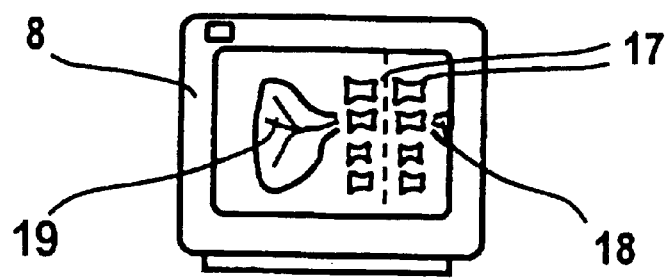
FIG. 5 shows a monitor image with a current transillumination image and with the shifted, first partial image in accordance with the invention.
Figure 6:
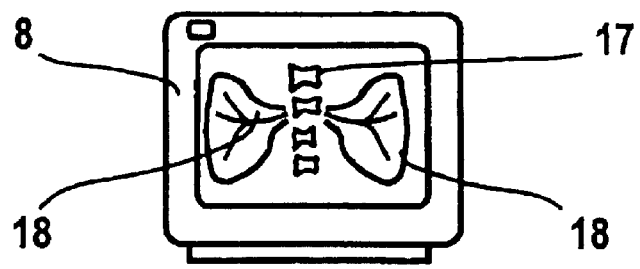
FIG. 6 shows a monitor image with an overall image from two partial images in accordance with the invention.

The inventive procedure of the apparatus according to FIG. 2 shall now be explained in greater detail on the basis of FIGS. 3 through 5. A first partial image with a part of a spinal column 17 and a right lung 18 is displayed as an X-ray image on the monitor 8 of FIG. 3. This is now stored in the first partial image memory 11 and is shifted by the shift device 12 so that the monitor image according to FIG. 4 is obtained. The shift ensued because the second exposure is intended to cover the left lung 19 that is to be registered together with the part 17 of the spinal column.

Subsequently, the second partial image is reproduced next to the shifted partial image in a transillumination (fluoroscopy) or as an exposure (static image), so that a monitor image according to FIG. 5 appears. A juncture of the second partial image to the first partial image shown at the edge now can be found easily by moving the apparatus and/or by moving the patient. It is not important to find an exact juncture; rather, it suffices to approximately find the position so that there is no gap (unimaged region) between the images. By virtue of the prominent parts of the spinal column 17 from the first exposure as well as from the second exposure that are visible on the monitor 8, the X-ray apparatus can be easily aligned such that the parts 17 of the spinal column exhibit the same height and the same alignment. This monitor image is generated by the mixing device 13. When enough exposures have been made, i.e. only the right and left lungs 18 and 19 are to be simultaneously played back on the monitor, then the arrangement for joining the partial images 15 can implement the matching of the two images such that the image reproduced in FIG. 6 is obtained. To this end, for example, "matching software" brings the images exactly together in X-Y direction—including rotation among other things—and also compensates for any exposure differences.

Figure 7:
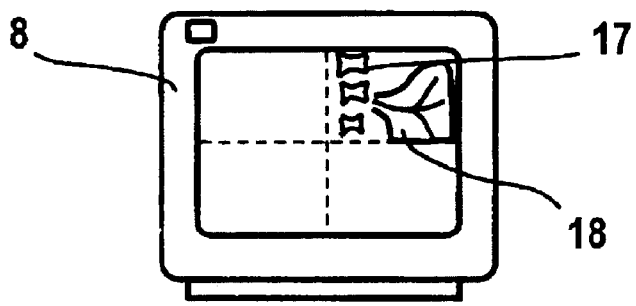
FIG. 7 shows a monitor image for four partial images with a shifted, first partial image in accordance with the invention.
Figure 8:
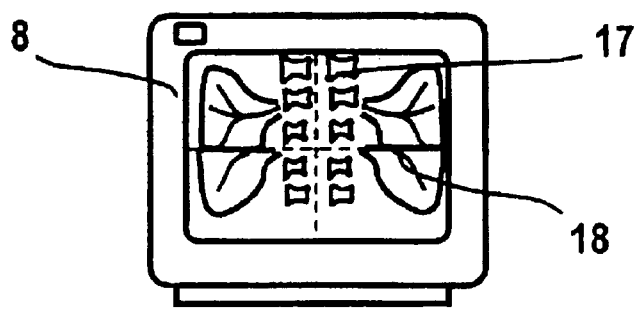
FIG. 8 shows monitor image with four shifted partial images in accordance with the invention.

When, in contrast, the X-ray detector 5 is so small that it cannot cover the lobes of the lung as a whole, then, for example, four exposures are produced that must be distributed on the monitor according to FIGS. 7 and 8. The first partial image is reproduced at the proper location in a window in FIG. 7. One proceeds as already set forth for producing the next partial image, and this is then reproduced in the region of the image on the monitor 8 that is allocated to it (FIG. 8). The further exposures are then produced in the same way, and are played back on the monitor 8 and subsequently correctly composed so that the image according to FIG. 6 again is obtained.

Single shots instead of a transillumination could also be made with minimum dose for the positioning.

A real image of the patient, a photograph, can also be employed in the same way for the selection of the correct exposure field when the real image is made in the exact projection corresponding to the X-ray exposure, for example by means of a depth diaphragm.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for producing an overall medical image from a plurality of partial images of an examination subject produced successively for common playback, comprising the following steps of:
   a) producing a first partial image with a medical image acquisition device;
   b) storing the first partial image;
   c) playing back at least a part of the first partial image that adjoins a second partial image to be produced of an exposure region;
   d) producing a survey image for the second partial image;
   e) simultaneously playing back the survey image and the first partial image in an adjustment image with overlapping regions adjoining one another;
   f) selecting a correct orientation of the exposure region for the second partial image based on said adjustment image;
   g) positioning the image acquisition device dependent on said orientation;
   h) producing a second partial image with said image acquisition device; and
   i) joining the first and second partial images to form an overall image.

2. A method as claimed in claim 1 comprising repeating steps (c) through (h) using said second partial image as said first partial image and using a further partial image as said second partial image.

3. A method as claimed in claim 1 comprising dividing said overall image into a plurality of windows and inserting said respective partial images into said windows with respectively correct orientations.

4. A method as claimed in claim 1 comprising producing a survey image in a transillumination mode.

5. A method as claimed in claim 1 comprising producing a survey image as a single shot in an exposure mode.

6. A method as claimed in claim 1 comprising generating a real image of said examination subject in a projection identical to a projection of said first partial image.

7. A diagnostic installation comprising:

an image acquisition device which produces a first partial image of a medical examination subject;

a first memory connected to said image acquisition device in which said first partial image is stored;

a playback device;

a shift device connected to said first memory and to said playback device for causing at least a portion of said first partial image, which adjoins a further partial image to be produced, and said playback device;

a mixing device connected to said image acquisition device and to said playback device for causing a survey image of said further partial image to be reproduced on said playback device in addition to said portion of said first partial image in a proper orientation relative to said portion of said first partial image;

said image acquisition device then obtaining said further partial image with said correct orientation; and an arrangement for joining said first partial image and said further partial image to form an overall image.

8. A diagnostic installation as claimed in claim 7 further comprising a control device for aligning said image acquisition device to a proper position for obtaining said further partial image.

* * * * *